United States Patent
Westlund et al.

(10) Patent No.: US 9,744,349 B2
(45) Date of Patent: Aug. 29, 2017

(54) MEDICAL LEAD AND IMPLANTATION

(75) Inventors: Randy W. Westlund, River Falls, WI (US); Mark C. Lynn, Circle Pines, MN (US)

(73) Assignee: Respicardia, Inc., Minnetonka, MN (US)

( * ) Notice: Subject to any disclaimer, the term of this patent is extended or adjusted under 35 U.S.C. 154(b) by 92 days.

(21) Appl. No.: 13/049,520

(22) Filed: Mar. 16, 2011

(65) Prior Publication Data

US 2012/0209284 A1 Aug. 16, 2012

Related U.S. Application Data

(60) Provisional application No. 61/441,559, filed on Feb. 10, 2011.

(51) Int. Cl.

| A61B 19/00 | (2006.01) |
|---|---|
| A61N 1/05 | (2006.01) |
| A61M 25/00 | (2006.01) |
| A61M 25/06 | (2006.01) |
| A61M 29/00 | (2006.01) |

(52) U.S. Cl.
CPC ......... *A61N 1/056* (2013.01); *A61M 25/0041* (2013.01); *A61M 25/0054* (2013.01); *A61M 25/0068* (2013.01); *A61M 25/0662* (2013.01); *A61M 25/0668* (2013.01); *A61M 29/00* (2013.01); *A61M 2025/0081* (2013.01)

(58) Field of Classification Search
CPC ......... A61N 1/05; A61N 1/056; A61B 19/00; A61B 5/042; A61B 5/0421; A61B 5/0422; A61B 5/6852; A61B 5/6855; A61M 25/0068; A61M 25/0041; A61M 25/0054; A61M 25/0662; A61M 2025/0081; A61M 29/00; A61M 25/0668
USPC ......... 606/129; 607/126, 116, 122; 600/585, 600/373, 381

See application file for complete search history.

(56) References Cited

U.S. PATENT DOCUMENTS

| 4,169,479 | A |   | 10/1979 | Muto |
|---|---|---|---|---|
| 4,306,562 | A | * | 12/1981 | Osborne ........................ 604/523 |
| 4,471,777 | A | * | 9/1984 | McCorkle, Jr. ................ 606/129 |
| RE31,855 | E | * | 3/1985 | Osborne ........................ 604/161 |
| 4,846,812 | A | * | 7/1989 | Walker et al. ................. 604/264 |
| 5,184,621 | A |   | 2/1993 | Vogel et al. |
| 5,312,355 | A | * | 5/1994 | Lee ................................. 604/160 |
| 5,423,876 | A | * | 6/1995 | Camps et al. .................. 607/116 |
| 5,489,225 | A | * | 2/1996 | Julian ............................. 439/837 |
| 5,531,781 | A |   | 7/1996 | Alferness et al. |
| 5,755,766 | A | * | 5/1998 | Chastain ................ A61N 1/056 600/381 |
| 5,769,875 | A | * | 6/1998 | Peckham et al. ................ 607/48 |
| 5,871,528 | A | * | 2/1999 | Camps et al. .................. 607/119 |
| 6,321,123 | B1 | * | 11/2001 | Morris et al. .................. 607/122 |
| 6,456,863 | B1 |   | 9/2002 | Levin et al. |

(Continued)

*Primary Examiner* — Amy R Weisberg
(74) *Attorney, Agent, or Firm* — Frank P. Piskolich

(57) ABSTRACT

A lead for navigating small vessels and a catheter system for implantation of leads into small vessels. Veins that return blood to the heart against the force of gravity often have valves in them to prevent backflow of deoxygenated blood. Leads and catheter systems in accordance with embodiments of the invention allow cannulation and lead implantation in small, tortuous, obstructed, and difficult to access veins enabling a range of stimulation and sensing applications.

9 Claims, 3 Drawing Sheets

(56) References Cited

U.S. PATENT DOCUMENTS

| | | | |
|---|---|---|---|
| 6,662,055 B1* | 12/2003 | Prutchi | 607/122 |
| 6,714,823 B1* | 3/2004 | De Lurgio et al. | 607/122 |
| 6,944,506 B1* | 9/2005 | Morgan et al. | 607/122 |
| 7,628,801 B2 | 12/2009 | Westlund et al. | |
| 7,647,115 B2 | 1/2010 | Levin et al. | |
| 7,647,124 B2* | 1/2010 | Williams | 607/122 |
| 7,699,809 B2* | 4/2010 | Urmey | 604/165.02 |
| 7,729,782 B2* | 6/2010 | Williams et al. | 607/122 |
| 7,747,323 B2 | 6/2010 | Libbus et al. | |
| 7,747,334 B2* | 6/2010 | Bly et al. | 607/122 |
| 7,787,946 B2 | 8/2010 | Stahmann et al. | |
| 7,792,591 B2* | 9/2010 | Rooney et al. | 607/116 |
| 8,086,314 B1 | 12/2011 | Kieval | |
| 8,090,451 B2* | 1/2012 | Tyson, Jr. | 607/122 |
| 8,131,372 B2 | 3/2012 | Levin et al. | |
| 8,200,336 B2 | 6/2012 | Tehrani et al. | |
| 8,244,378 B2* | 8/2012 | Bly et al. | 607/127 |
| 8,255,056 B2 | 8/2012 | Tehrani | |
| 8,280,513 B2 | 10/2012 | Tehrani et al. | |
| 8,290,595 B2 | 10/2012 | Kieval et al. | |
| 8,348,941 B2 | 1/2013 | Tehrani | |
| 8,463,401 B2 | 6/2013 | Jones et al. | |
| 2002/0049485 A1* | 4/2002 | Smits | 607/122 |
| 2002/0165535 A1 | 11/2002 | Lesh et al. | |
| 2003/0028232 A1* | 2/2003 | Camps et al. | 607/122 |
| 2003/0181967 A1* | 9/2003 | Dadd et al. | 607/122 |
| 2004/0064024 A1* | 4/2004 | Sommer | 600/374 |
| 2004/0236396 A1* | 11/2004 | Coe et al. | 607/116 |
| 2005/0054989 A1* | 3/2005 | McGuckin et al. | 604/264 |
| 2005/0070986 A1* | 3/2005 | Tockman et al. | 607/122 |
| 2005/0256503 A1* | 11/2005 | Hall | 604/523 |
| 2005/0288759 A1 | 12/2005 | Jones et al. | |
| 2006/0135962 A1* | 6/2006 | Kick et al. | 606/108 |
| 2006/0142783 A1* | 6/2006 | Lewis et al. | 606/127 |
| 2006/0247750 A1* | 11/2006 | Seifert et al. | 607/122 |
| 2007/0043390 A1* | 2/2007 | Neilan | 606/200 |
| 2007/0055334 A1* | 3/2007 | Haldeman et al. | 607/122 |
| 2007/0088417 A1* | 4/2007 | Schouenborg | 607/116 |
| 2007/0282412 A1* | 12/2007 | Soltis et al. | 607/119 |
| 2008/0009929 A1* | 1/2008 | Harris et al. | 607/116 |
| 2008/0071341 A1* | 3/2008 | Goode et al. | 607/122 |
| 2008/0188867 A1* | 8/2008 | Ignagni et al. | 606/129 |
| 2008/0243081 A1* | 10/2008 | Nance et al. | 604/164.03 |
| 2009/0036947 A1* | 2/2009 | Westlund et al. | 607/42 |
| 2010/0076534 A1* | 3/2010 | Mock | 607/116 |
| 2010/0152748 A1* | 6/2010 | Penner et al. | 606/129 |
| 2010/0268312 A1* | 10/2010 | Wallace et al. | 607/137 |
| 2011/0009934 A1* | 1/2011 | Conger | 607/116 |
| 2011/0160820 A1* | 6/2011 | Jackson et al. | 607/116 |
| 2011/0160822 A1* | 6/2011 | Jackson et al. | 607/116 |
| 2011/0160825 A1* | 6/2011 | Haarer et al. | 607/116 |
| 2011/0160830 A1* | 6/2011 | Morris et al. | 607/119 |
| 2011/0301593 A1* | 12/2011 | Teichman et al. | 606/41 |
| 2012/0130269 A1* | 5/2012 | Rea | A61B 5/0488 600/554 |
| 2012/0130397 A1* | 5/2012 | Reddy et al. | 606/129 |

* cited by examiner

MEDICAL LEAD AND IMPLANTATION

CLAIM OF PRIORITY

This application claims the benefit and incorporates as relevant by reference U.S. Provisional Application 61/441,559 filed Feb. 10, 2011 entitled "Venous Access Catheter."

BACKGROUND

Electrical stimulation of nervous structures has been used to treat pain, breathing disorders, neural disorders, and other conditions. Implantation of electrodes configured as cuffs, paddles, or other structures has typically been a delicate surgical process with potential for nerve damage during the procedure, or as implanted stimulation devices migrate or contact delicate nervous tissue.

SUMMARY

Nerves often course adjacent blood vessels or other lumens in anatomical structures called "complexes." For example, the vagus complex in the cervical region is comprised of the vagus nerve, the external jugular vein, and the carotid artery. Vagal structures and others are relatively large, but complexes are more often rather small. For example the phrenic complex comprised of the phrenic nerve, the pericardiophrenic vein, and the pericardiophrenic artery is much smaller.

When such a complex is located below the heart, the venous system has valves that facilitate return blood flow to the heart and prevent backflow of deoxygenated blood. The placement of a lead in such a small vessel and/or a vessel with valves or other impediments is a challenge.

In one embodiment in accordance with the invention, a medical electrical lead has an elongate lead body with a lead body diameter defining a lumen therein, the lumen having a lumen diameter. There is a tapered tip at a distal end of the lead, and the tip tapers from about the lumen diameter to the lead body diameter over a length greater than the difference between the lumen diameter and the lead body diameter. In other embodiments, the tip tapers from about the lumen diameter to the lead body diameter over a length greater than twice, three times, and five times the difference between the lumen diameter and the lead body diameter.

In another embodiment in accordance with the invention, a medical electrical lead has lumen having a constricted section with a constricted lumen diameter extending a length from the tip before transitioning to the nominal lumen diameter.

In yet another embodiment in accordance with the invention, a catheter system includes a catheter body having a lumen therein. The catheter body has a proximal end and a distal end, and the catheter body has a first catheter body stiffness along the proximal portion and transitions to a less stiff second catheter body stiffness at a transition point proximate the distal end of the catheter. The catheter system of this embodiment has a hook portion of the catheter body at the distal end so that the end of the catheter body is angled relative to a portion of the catheter nearest the hook by at least 80 degrees.

In yet another embodiment in accordance with the invention, a catheter system includes a catheter body having a lumen therein. The catheter body has a proximal end and a distal end, and the catheter body has a first catheter body stiffness along the proximal portion and transitions to a less stiff second catheter body stiffness at a transition point proximate the distal end of the catheter. The catheter system of this embodiment has a hook portion of the catheter body at the distal end so that the end of the catheter body is angled relative to a portion of the catheter nearest the hook by at least 80 degrees. This embodiment further includes preformed bends in the catheter body configured support a right subclavian vein method of approaching the left pericardiophrenic vein by engaging the venous walls in the subclavian veins in order to provide adequate support for the delivery of a lead. In some embodiments, a preformed curve is configured to nest at the junction of the right and left brachiocephalic veins to stabilize the catheter.

In yet another embodiment in accordance with the invention, a catheter system includes a catheter body having a lumen therein. The catheter body has a proximal end and a distal end, and the catheter body has a first catheter body stiffness along the proximal portion and transitions to a less stiff second catheter body stiffness at a transition point proximate the distal end of the catheter. The catheter system of this embodiment has a hook portion of the catheter body at the distal end so that the end of the catheter body is angled relative to a portion of the catheter nearest the hook by at least 80 degrees. This embodiment further includes preformed bends in the catheter body configured support a left subclavian vein method of approaching the left pericardiophrenic vein by engaging the venous walls in the left subclavian vein in order to provide adequate support for the delivery of a lead.

In yet another embodiment in accordance with the invention, a catheter system includes a catheter body having a lumen therein. The catheter body has a proximal end and a distal end, and the catheter body has a first catheter body stiffness along the proximal portion and transitions to a less stiff second catheter body stiffness at a transition point proximate the distal end of the catheter. The catheter system of this embodiment has a hook portion of the catheter body at the distal end so that the end of the catheter body is angled relative to a portion of the catheter nearest the hook by at least 80 degrees. In this embodiment the transition point is within the hook portion of the catheter. Some embodiments include a second stiffness transition point about one-sixth of the length of the catheter from the distal end of the catheter. Some embodiments include a third stiffness transition point about one-third of the length of the catheter from the distal end of the catheter.

In yet another embodiment in accordance with the invention, a catheter system includes a catheter body having a lumen therein. The catheter body has a proximal end and a distal end, and the catheter body has a first catheter body stiffness along the proximal portion and transitions to a less stiff second catheter body stiffness at a transition point proximate the distal end of the catheter. The catheter system of this embodiment has a hook portion of the catheter body at the distal end so that the end of the catheter body is angled relative to a portion of the catheter nearest the hook by at least 80 degrees. This embodiment further includes a dilator configured to slidably fit within the catheter lumen.

In yet another embodiment in accordance with the invention, a catheter system includes a catheter body having a lumen therein. The catheter body has a proximal end and a distal end, and the catheter body has a first catheter body stiffness along the proximal portion and transitions to a less stiff second catheter body stiffness at a transition point proximate the distal end of the catheter. The catheter system of this embodiment has a hook portion of the catheter body at the distal end so that the end of the catheter body is angled relative to a portion of the catheter nearest the hook by at least 80 degrees. This embodiment further includes a dilator configured to slidably fit within the catheter lumen. In some embodiments, the dilator body has a first dilator body stiffness along the proximal portion and transitions to a less stiff second dilator body stiffness at a transition point proximate the distal end of the dilator. Some embodiments include a second stiffness transition point about one-sixth of the length of the dilator from the distal end of the dilator. Some embodiments include a third stiffness transition point about one-third of the length of the dilator from the distal end of the dilator.

In still another embodiment in accordance with the invention, a method of implanting a lead in a small vein includes the steps of advancing a catheter having a hook portion at its distal end through an access vein, advancing the catheter into the ostium of a smaller vein, utilizing a preformed bend in the catheter to stabilize the catheter in the ostium of the smaller vein by engaging the preformed bend with the access vein wall, and advancing a lead through the stabilized catheter and into the smaller vein to a target location. This embodiment may be used, for example, where the access vein is a brachiocephalic vein and the smaller vein is the left pericardiophrenic vein.

In still another embodiment in accordance with the invention, a method of implanting a lead in a small vein includes the steps of advancing a catheter having a hook portion at its distal end through an access vein, advancing the catheter into the ostium of a smaller vein, utilizing a preformed bend in the catheter to stabilize the catheter in the ostium of the smaller vein by engaging the preformed bend with the access vein wall, advancing a guide wire through the catheter into the smaller vein proximate the target location, advancing a dilator over the guide wire to clear obstructions from the smaller vein, retracting the dilator from the catheter and advancing a lead through the stabilized catheter and into the cleared smaller vein to a target location.

Embodiments of the present invention include electrode bearing leads configured for transluminal stimulation of tissues, catheters and lead deployment systems capable of implanting such leads in a target lumen, and methods of employing leads and related deployment systems.

DETAILED DESCRIPTION

Figure 1:
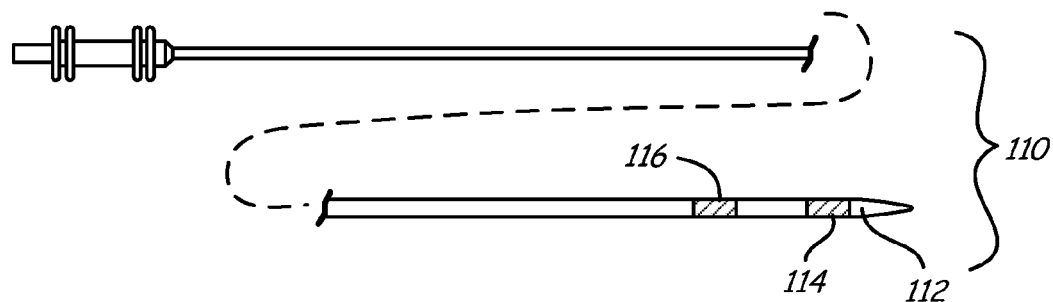
FIG. 1 is a plan view of a lead in accordance with embodiments of the invention.

FIG. 1 is a plan view of a lead in accordance with embodiments of the invention. An over the wire open lumen lead is illustrated at 110 that includes a frusto-conical tapered tip 112 that aids in navigating the lead past valves and into small diameter veins. In one exemplary embodiment, the open lumen lead accepts a 0.014 inch diameter lead wire and the interior diameter of the lumen is in a range of between about 0.018 inches and 0.020 inches. An exemplary outer diameter of the lead is about 0.05 inches. A lead and guide wire of these dimensions and configurations may be able to navigate venous valves and also veins having a diameter in the range of about 1 mm to about 3 mm, but it is also contemplated that designs having other dimensions and configurations would occur to those of skill in the art upon reading this disclosure.

The lead may be constructed of a polyurethane lead body insulating layer that increases the stiffness of the lead as compared to other leads. The increased stiffness of the lead allows for better navigation, for instance, when employed retrograde in veins to get around the valves. The tapered tip 112 allows the lead to more easily navigate the venous valves because the end of the lead has a diameter that is relatively close to the diameter of the lead wire and the tip 112 smoothly transitions to the diameter of the main portion of the lead.

The distal end of the lead of FIG. 1 includes spaced apart electrodes 114 and 116, where the electrodes 114 and 116 are located on the lead proximal the tapered tip 112. Although two electrodes are illustrated, an alternative configuration of the distal end 112 of the lead includes five electrodes, where three electrodes are stimulation electrodes and two electrodes are sensing electrodes. Providing multiple stimulation electrodes allows the location of the stimulation to be changed to capture the target tissues and reduce the likelihood of spurious or unwanted stimulation of other nerves. Multiple variations of this design are possible, however a lead having a distal end with one or more electrodes is contemplated.

In one embodiment the tapered distal tip 112 is hot molded on the end of a polyurethane lead out of the underlying polyurethane material. The polyurethane material provides the required rigidity to navigate past the venous valves, if present, and also provides a uni-body or monolithic lead construction that requires no joints or bonding of two materials together.

Figure 2:
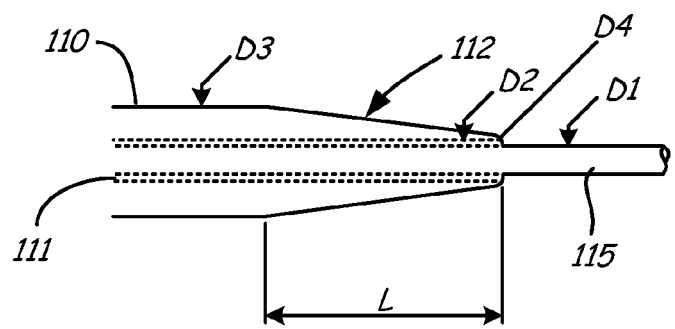
FIG. 2 is a plan view of a lead in accordance with embodiments of the invention.

FIG. 2 is a plan view of a lead in accordance with embodiments of the invention. Referring to FIG. 2, a cross-section of an embodiment of a tapered tip 112 of a lead is illustrated. The central lumen 111 diameter D2 is only slightly larger than the diameter D1 of the guide wire 115, and is sized to allow passage of the lead 110 over the guide wire 115 with minimal deviation of the lead 110 from the wire 115. An outer diameter D4 of the lead 110 at the very distal end is relatively close to the diameter D1 of the guide wire 115 such that a difference between the diameters D1 and D4 is minimized. With the diameter D4 of the distal end 112 being similar to the diameter D1 of the guide wire 115, the lead 110 is able to closely follow the path of the guide wire 115 around bends in a lumen such as a vein as the lead 110 is advanced over a wire 115. This is particularly advantageous when navigating tortuous venous structures that include valves. The diameter of the tapered tip 112 smoothly transitions to diameter D3 from D4 over a length L of the tip 112 such that the lead 110 is able to smoothly pass through bends, valves, and other challenging pathways.

In some embodiments in accordance with the invention, length L is greater than the difference between lumen diameter D2 and lead diameter D3. As an example, if the length L were equal to the difference between lumen diameter D2 and lead diameter D3, the taper of the tip would be nominally 45 degrees.

Figure 3:
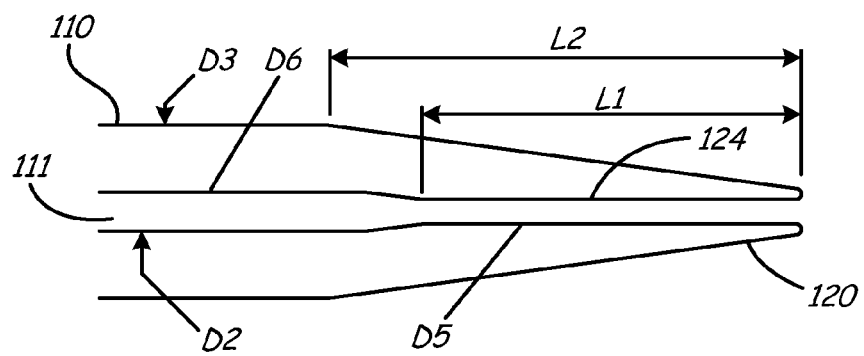
FIG. 3 is a plan view of a lead in accordance with embodiments of the invention.

Referring to FIG. 3, another cross-section of an embodiment of a distal tapered tip 120 of a lead 110 is illustrated. The configuration of the lumen 111 results in a lumen diameter that transitions from constricted section 124 having a constricted diameter D5 to the nominal diameter D6 of the lumen 111. The diameter D5 of the constricted section lumen can extend a length L1 and then transition to the diameter D6 at L2. Alternatively the diameter can gradually taper from D5 to D6 over the length L1 or the length L2. The distal tip 112 with different diameters D5 and D6 of the lumen 111 ensures that the lead 110 has adequate clearance between the guide wire 115 and the lumen 111 to easily pass the lead 110 over the guide wire 115 while minimizing the diameter D4 of the outer surface of the tip 120 to ensure that the lead 110 can pass through valves and around bends in lumens and closely track the guide wire 115 as it is passed over it.

The utilization of the lead 110 with the tapered tip configurations in accordance with embodiments of the invention allows for deployment of leads in small vessels with tortuous physiology or obstructions such as valves. Such leads can be employed to stimulate nerves or other tissues from lumens of relatively small diameters that were previously not able to be cannulated or to have leads installed in them.

Figure 4:
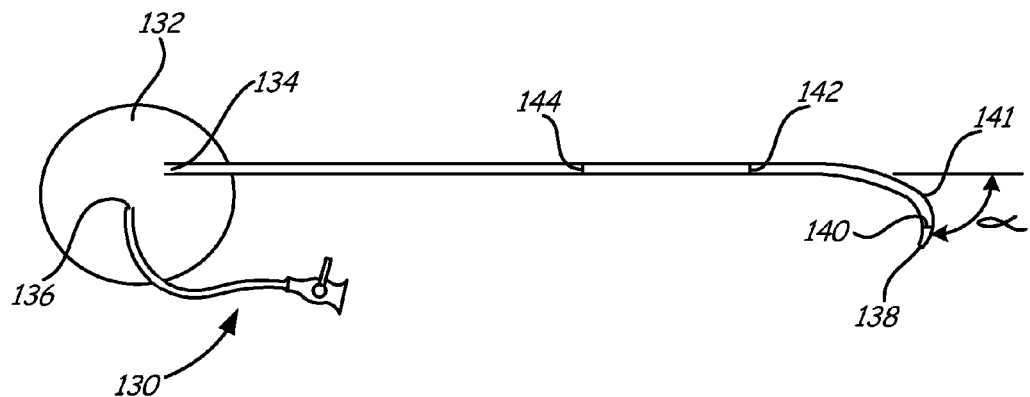
FIG. 4 is a plan view of a catheter in accordance with embodiments of the invention.

FIG. 4 is a plan view of a catheter in accordance with embodiments of the invention. Referring to FIG. 4, a catheter 130 is illustrated for implanting a lead into a vein, possibly proximate a nerve, such as a pericardiophrenic vein proximate a phrenic nerve. The catheter 130 includes a splittable hemostasis valve system 132 at a proximal end 134. Splittable hemostasis valve systems are known in the art and an exemplary description can be found in U.S. Pat. No. 5,125,904 to Lee. The proximal end 134 may optionally include a side port 136 that can be utilized to deliver of contrast medium. The catheter 130 may optionally be configured to have a slittable hub that accepts a hemostatic valve. The hemostatic valve may be of a configured to pass over the electrical terminal pin of a stimulation or sensing lead.

A distal end 138 of the catheter may include different materials, thicknesses, and transitions along its length. The materials and thicknesses affect the catheter stiffness and provide for a smooth transition that results in a soft and flexible tip while the body of the catheter is stiff enough to be pushed through the venous system and to withstand torque if necessary for positioning or advancing the catheter. Exemplary catheter stiffness transition points are located at 140, 142, and 144 which are at 0.5, 6 and 10 centimeters, respectively, from the distal end 138 of a catheter 130, where the catheter 130 has a length of 35 cm. However, other transition locations are also contemplated as well as catheters of different lengths.

The body of the catheter 130 contains a braided material around the circumference thereof to improve the performance of the catheter 130 when subjected to a torque. An inner diameter of an exemplary embodiment of the catheter may be sized to accept a 4 Fr lead. The outer wall of such an embodiment may be about 5 Fr to about 6 Fr such that the wall can contain the braided material and provide the necessary performance when the catheter is subjected to a torque. The distal end 138 of this exemplary catheter 130 may be tapered to less than 5 Fr for cannulation into the venous system.

The distal end 138 may be configured to have a hook 141 having an angle α ranging from about 90 degrees to about 130 degrees which aids in cannulation of small veins that are generally skew to a larger vein used for catheterization. One example of this anatomical relationship is the junction of the left pericardiophrenic vein with the left brachiocephalic vein. The external and internal surfaces of the catheter 130 may be treated with lubricious coatings that facilitate lead and wire passage (not shown) through the catheter as well as catheter advancement.

Figure 5:
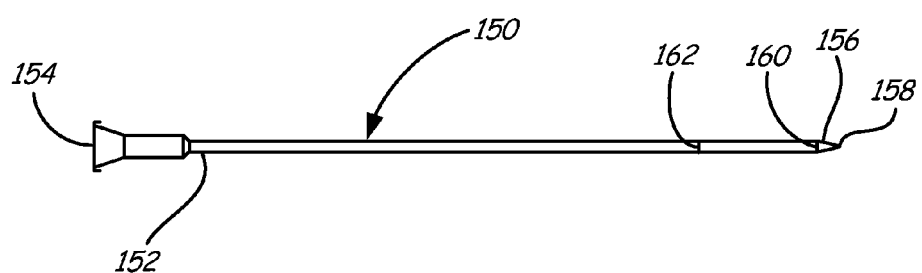
FIG. 5 is a plan view of a dilator in accordance with embodiments of the invention.

FIG. 5 is a plan view of a dilator in accordance with embodiments of the invention. The tapered guide catheter 130 is introduced into the venous system utilizing a catheter dilator 150 as illustrated in FIG. 5. The dilator in one example is about 45 cm which is about 10 centimeters longer than the exemplary catheter 130 described above. However, other lengths of dilators and the catheters are also contemplated. The dilator 150 is utilized to gain entry into the venous system through percutaneous methods.

The dilator 150 is sized to slide within the catheter 130. The proximal end 152 of the dilator 150 is fitted with a standard hub 154 that allows the dilator 150 to be flushed. The lumen of the dilator 150 of one embodiment is sized to accept a 0.038" diameter guide wire (not shown). However, the size of the lumen of the dilator 150 can vary to accept different diameter guide wires.

The dilator can also have a tapered tip 156 at a distal end 158 with material transition points 160 and 162 that result in a soft and flexible tip 156 while the body of the dilator is stiff enough to manipulate effectively within the catheter and beyond. FIG. 5 illustrates locations 160 and 162 for transitions of the stiffness, such as 0.75 cm and 5 cm, respectively, from the distal end 158. However, the locations of the transitions can vary.

The length of the soft tip 158 of the dilator 150 is proportional to the length of the soft tip 138 of the catheter 130. The soft tip 158 of the dilator 150 allows the dilator 150 to pass through the catheter tip 138 without substantial deformation of the shape of the catheter 130.

Figure 6:
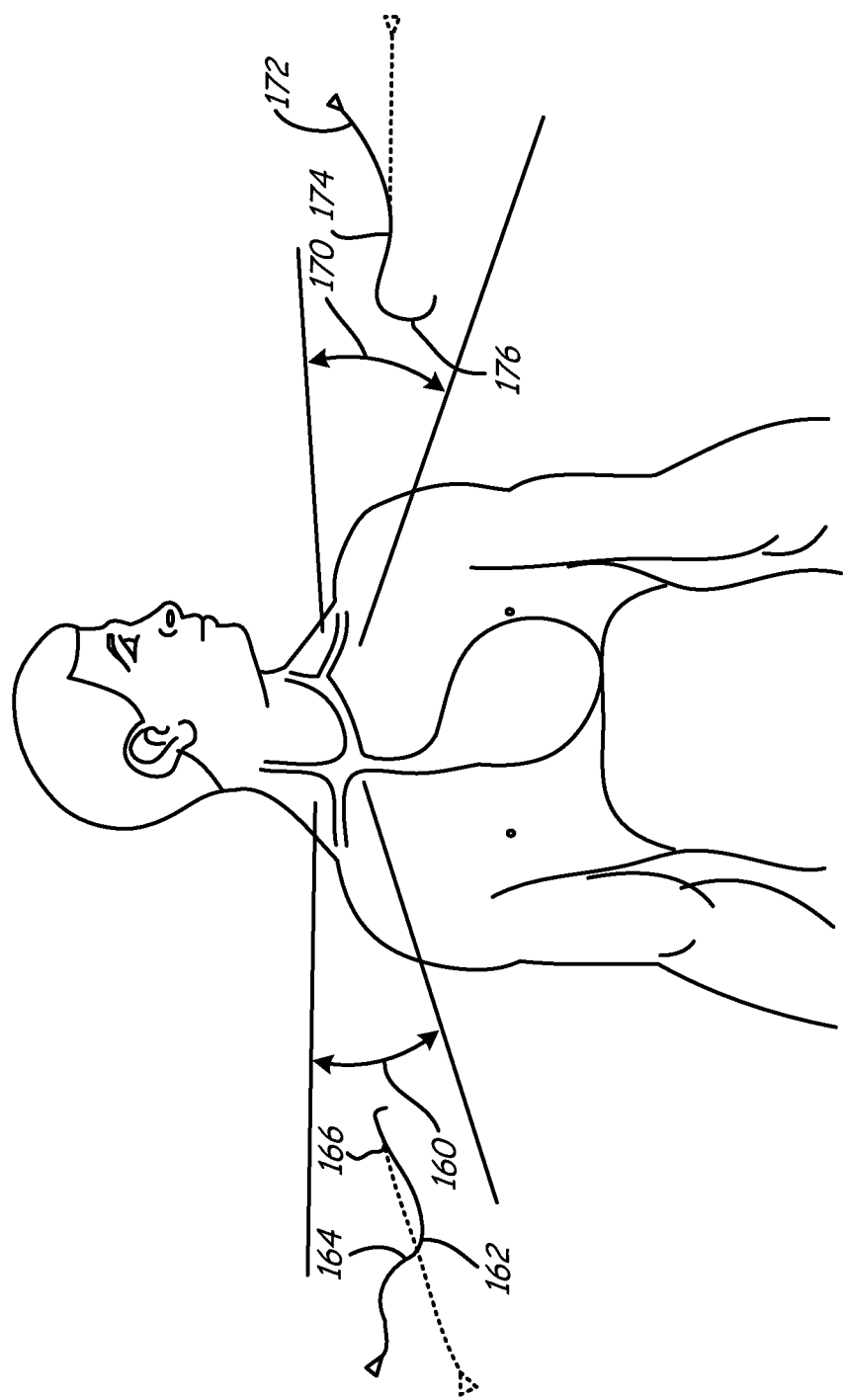
FIG. 6 is a schematic view of catheters in accordance with embodiments of the invention placed in context of a patient's body.

FIG. 6 is a schematic view of catheters in accordance with embodiments of the invention placed in context of a patient's body. FIG. 6 illustrates one application of a system in accordance with embodiments of the invention that includes a right subclavian vein method of approaching the left pericardiophrenic vein at 160. Using the right subclavian vein as the entry to the circulatory system, access to the left pericardiophrenic vein is obtained utilizing a shape 162 of the catheter 160. The catheter 160 enters the right subclavian vein and passes through the right brachiocephalic vein. The shape 162 then transitions into the left brachiocephalic vein in order to gain access to the left pericardiophrenic vein.

The shape 162 comprises two pre-formed curves 164 and 166 which facilitate access and provide stability of the catheter 160 during deployment of the lead. Curves 164 and 166 engage the venous walls in the subclavian veins in order to provide adequate support for the delivery of the lead. The curved tip of the catheter may work in conjunction with the curves 164 and 166 to provide a stable catheter platform for delivering the lead. For example, a 90 degree hook 141 (FIG. 4) may be used to enter the ostium of the left pericardiophrenic vein. As a lead is advanced through the catheter and into the vein, resistance to the lead is transmitted as force to the catheter at curve 166, which engages the left brachiocephalic vein and stabilizes the catheter allowing the lead to be pushed into the pericardiophrenic vein. Curve 164 may help facilitate crossover from the right brachiocephalic vein to the left brachiocephalic vein as the catheter is advanced. The curve may then "nest" at the junction of the right and left brachiocephalic veins to further stabilize the catheter as the lead or wire is advanced into the vein.

Veins that allow blood to return to the heart in an upward flow relative to gravity may have venous valves within them. These valves can restrict access by leads, catheters, and other intravenous devices, especially in smaller bore veins.

Methods in accordance with embodiments of the invention allow for cannulation of these veins through the use of a guide wire 115, catheter 130, and dilator 150. In one embodiment, a catheter in accordance with embodiments of the invention is deployed proximate a target location in the venous system. A guide wire is fed through the catheter to a target location. If possible, a lead in accordance with embodiments of the invention is fed over the wire until it is implanted at the desired location. If tortuous vein geometry or valves make implantation of the lead difficult or impossible, a dilator in accordance with embodiments of the invention can be fed over the wire instead of the lead and can push through the valves or tortuosity to create a path through which the lead can be implanted. The dilator is then removed from the catheter and the lead is implanted through the pathway created by the dilator.

A left subclavian vein method of approaching the left pericardiophrenic vein is also illustrated in FIG. 6 at 170. The left subclavian vein method operates similarly to the right subclavian method, except that the shape 172 of the catheter 170 utilizing the left subclavian method comprises two curves 174 and 176 where 176 engages the junction of the left internal jugular vein and the left brachiocephalic vein while the catheter is engaged at the ostium of the pericardiophrenic vein to support the lead's delivery. The hook 141 of an embodiment configured for a left subclavian approach to the left pericardiophrenic vein through the left brachiocephalic vein may be on the order of 130 degrees, for example. Other hook angles may occur to those of skill in the art upon reading this disclosure.

Although the present invention has been described with reference to preferred embodiments, workers skilled in the art will recognize that changes may be made in form and detail without departing from the spirit and scope of the invention.

What is claimed is:

1. A medical electrical lead comprising:
   a. an elongate lead body with a lead body diameter; and
   b. a frustoconical tip extending from the elongate lead body and positioned at a distal end of the lead;
   c. wherein the lead body and the frustoconical tip define a lumen therein, the lumen having a first portion having a primary lumen diameter, a second portion having a smaller secondary lumen diameter proximate the distal end of the lead, and an intermediate portion that connects the first portion and the second portion, the intermediate portion comprising a tapered lumen surface that gradually decreases from the primary lumen diameter to the secondary lumen diameter;
   d. wherein an outside diameter of the frustoconical tip tapers from the lead body diameter to about the secondary lumen diameter at the distal end;
   e. wherein the intermediate portion and the second portion of the lumen are positioned inside the frustoconical tip; and
   f. wherein the intermediate portion extends for a length greater than a difference between the primary lumen diameter and the lead body diameter.

2. The medical electrical lead of claim 1, wherein the frustoconical tip tapers from the lead body diameter to about the secondary lumen diameter over a length greater than twice the difference between the primary lumen diameter and the lead body diameter.

3. The medical electrical lead of claim 1, wherein the frustoconical tip tapers from the lead body diameter to about the secondary lumen diameter over a length greater than three times the difference between the primary lumen diameter and the lead body diameter.

4. The medical electrical lead of claim 1, wherein the frustoconical tip tapers from the lead body diameter to about the secondary lumen diameter over a length greater than five times the difference between the primary lumen diameter and the lead body diameter.

5. The medical electrical lead of claim 1 and wherein the frustoconical tip comprises a wall having a substantially annular cross-section, wherein the wall has a thickness that decreases from a proximal end of the frustoconical tip to a distal end of the frustoconical tip.

6. A medical electrical lead comprising:
   a. an elongate lead body extending from a proximal end to a distal end; and
   b. a frustoconical tip having a proximal end and a distal end, wherein the proximal end of the frustoconical tip extends from the distal end of the lead body,
   c. wherein the lead body and the frustoconical tip define a lumen therein, the lumen having a first portion having a primary lumen diameter, a second portion having a smaller secondary lumen diameter, and an intermediate portion having a tapered lumen surface that gradually decreases from the primary lumen diameter to the secondary lumen diameter; the lead body having the first portion of the lumen, the frustoconical tip having the second portion of the lumen and the intermediate portion of the lumen, wherein the second portion of the lumen is in communication with the first portion of the lumen;
   d. wherein the frustoconical tip comprises a wall, wherein the wall has a thickness that decreases from the proximal end of the frustoconical tip to the distal end of the frustoconical tip and wherein the second portion extends for a length greater than a difference between the primary lumen diameter and the lead body diameter.

7. The medical electrical lead of claim 6, wherein the frustoconical tapers from the lead body diameter to about the secondary lumen diameter over a length greater than twice the difference between the primary lumen diameter and the lead body diameter.

8. The medical electrical lead of claim 6, wherein the frustoconical tip tapers from the lead body diameter to about the secondary lumen diameter over a length greater than three times the difference between the primary lumen diameter and the lead body diameter.

9. The medical electrical lead of claim 6, wherein the frustoconical tip tapers from the lead body diameter to about the secondary lumen diameter over a length greater than five times the difference between the primary lumen diameter and the lead body diameter.

* * * * *